United States Patent [19]

Yunker et al.

[11] Patent Number: 4,703,010

[45] Date of Patent: Oct. 27, 1987

[54] ELECTROLYTIC BIOREACTOR ASSEMBLY AND METHOD

[75] Inventors: Stanley B. Yunker, Danville, Pa.; John M. Radovich, Bend, Oreg.

[73] Assignee: The Board of Regents for the University of Oklahoma, Norman, Okla.

[21] Appl. No.: 859,007

[22] Filed: May 2, 1986

[51] Int. Cl.$^4$ .............................................. C12N 13/00
[52] U.S. Cl. ..................................................... 435/173
[58] Field of Search ............... 435/173, 287, 291, 289; 204/131

[56] References Cited

U.S. PATENT DOCUMENTS

| | | | |
|---|---|---|---|
| 3,919,052 | 11/1975 | Fresnel et al. | 435/173 |
| 4,152,215 | 5/1979 | Yoshino et al. | 435/289 |
| 4,264,740 | 4/1981 | Christ et al. | 435/289 |
| 4,288,544 | 9/1981 | Suzuki et al. | 435/39 |

FOREIGN PATENT DOCUMENTS 59-162493  9/1984  Japan .................................. 204/131

OTHER PUBLICATIONS

Oral Presentation Script and Slide Show Prints from Ann. Meeting of Am. Soc. for Microbiology, Dallas, Tex., Apr. 1981, by Stan B. Yunker.
G. Denisov, B. Kovrov, I. Trubachev, I. Gribovskaya, A. Stephen and O. Novoselova "Composition of a Growth Medium for Continuous Cultivation of T. Ferrooxidans", *Mikrobiologiya*, vol. 49, No. 3, pp. 473-478 (May-Jun. 1980).
B. Kovrov, G. Denisov and L. Sekacheva, "Effect of Concentration of Ferrous Iron on its Rate of Oxidation by T. Ferrooxidans", *Mikrobiologiya*, vol. 47, No. 3, pp. 400-402 (May-Jun. 1978).
N. Kinsel and W. Umbreit, "Method for Electrolysis of Culture Medium to Increase Growth of the Sulphur-Oxidizing Iron Bacterium Ferrobacillus Sulfooxidans", *J. Bacteriol.*, vol. 87, pp. 1243-1244 (1964).

*Primary Examiner*—Samuel Scott
*Assistant Examiner*—Allen J. Flanigan
*Attorney, Agent, or Firm*—Dunlap, Codding & Peterson

[57] ABSTRACT

An electrolytic bioreactor, assembly and method for growing organisms capable of oxidizing metal sulfides. The reactor comprises a vessel defining an anode chamber for housing an anode, and a cultivation chamber, for housing a cathode and a culture solution, a selective barrier between such chambers, which is impermeable to the organisms and to cations, and a receptacle defining a pH control chamber for receiving samples of culture solution from the cultivation chamber so that such samples are insulated from electric current within the cultivation chamber. Preferably, the capacity of the anode chamber is about 1% to about 3% of the cultivation chamber. In accordance with the method of the present invention during operation of the reactor assembly, the pH of the culture solution is controlled by circulating samples through the pH control chamber.

14 Claims, 5 Drawing Figures

ELECTROLYTIC BIOREACTOR ASSEMBLY AND METHOD

FIELD OF THE INVENTION

The present invention relates generally to electrolytic bioreactors and methods for growing chemolithotrophic organisms.

SUMMARY OF THE INVENTION

An electrolytic bioreactor comprising a reaction vessel defining a cultivation chamber, adapted for containing a culture solution and a cathode, and an anode chamber disposed in fluid communication with the cultivation chamber, such anode chamber being adapted for containing an electrolyte solution and an anode; means for mounting a selective barrier between the anode chamber and the cultivation chamber so that the selective barrier will separate the anode chamber from the cultivation chamber but will allow fluid communication therebetween; and a receptacle defining a pH control chamber adapted for receiving samples of the culture solution from the cultivation chamber and connectable by a conduit to the cultivation chamber so that the solution samples within the pH control chamber are insulated from electric current passing through the cultivation chamber.

The present invention further comprises an electrolytic bioreactor assembly for growing chemolithotrophic organisms, comprising a reaction vessel defining a cultivation chamber, adapted for containing a culture solution, and an anode chamber disposed in fluid communication with the cultivation chamber, such anode chamber being adapted for containing an electrolyte solution; a cathode disposed within the cultivation chamber; an anode disposed within the anode chamber; a selective barrier separating the anode chamber from the cultivation chamber, such barrier being substantially impermeable to the organisms and to cations; means for establishing a potential difference between the cathode and the anode; and means for maintaining the solution within the cultivation chamber at a selected pH. The pH maintenance means comprises a receptacle defining a pH control chamber, such receptacle adapted for receiving samples of culture solution; means for circulating samples of culture solution from the cultivation chamber through the pH control chamber so that the culture solution samples within the pH control chamber are insulated from electric current within the cultivation chamber; means for monitoring the pH of the culture solution sample within the pH control chamber; and means for adjusting the pH of the culture solution within the pH control chamber, such pH adjusting means being responsive to the pH monitoring means.

The present invention further comprises a method for growing chemolithotrophic organisms capable of oxidizing metal sulfides. The method comprises contacting the organisms with culture solution comprising metal sulfide substrate within a cultivation chamber of an electrolytic bioreactor assembly wherein a cathode is disposed within the cultivation chamber and wherein an anode is disposed within an anode chamber containing an electrolyte solution, such anode chamber being in fluid communication with the cultivation chamber and separated therefrom by a selective barrier characterized by being substantially impermeable to cations and to the organisms; electrolyzing the culture solution and the organisms; and maintaining the culture solution at a selected pH during electrolysis by circulating samples of the culture solution through a pH control chamber, so that the culture solution samples within the pH control chamber are insulated from electric current within the cultivation chamber, monitoring the pH of the culture solution samples in the pH control chamber, and adjusting the pH of the culture solution samples in the pH control chamber in response to such monitoring.

DETAILED DESCRIPTION OF THE PREFERRED EMBODIMENT

Figure 1:
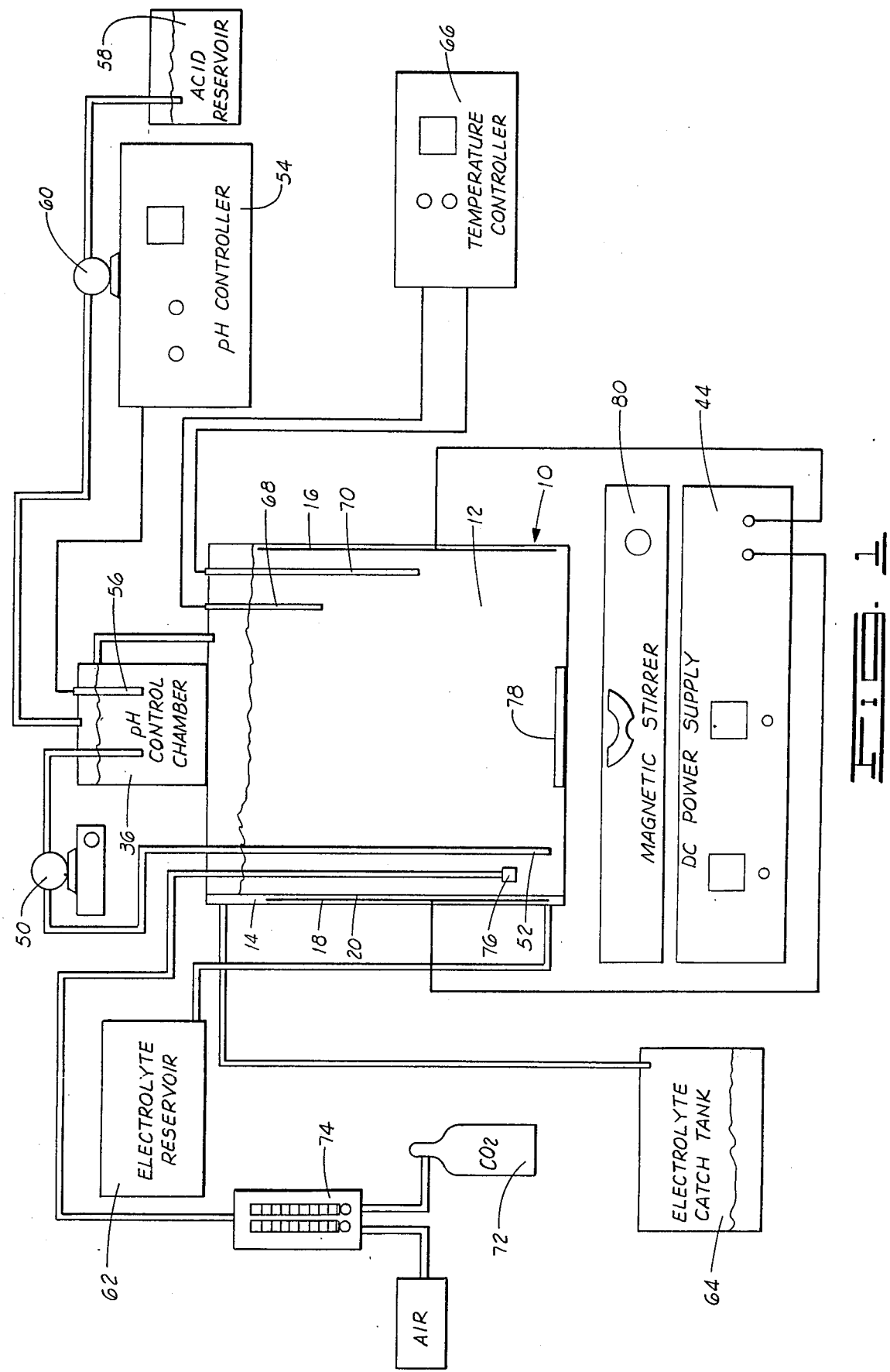
FIG. 1 is a semi-schematic diagram of the electrolytic bioreactor assembly of the present invention.

The importance of coal as an energy source inevitably will increase as the availability of other fossil fuels decreases. In addition to its significance as a fuel source, coal continues to be important industrially in the manufacture of iron and steel. Unfortunately, much of the coal mined in this country has a significant sulfur content. The presence of sulfur in coal is undesirable for at least two reasons. First, sulfur is an undesirable element in iron and steel. Second, the combustion of sulfur-containing coal results in the emission of sulfur oxides. Sulfur oxides are major atmospheric pollutants which presently are the subject of federal regulation. These pollutants represent a health hazard to the public and also can cause serious physical damage to surrounding structures.

For these reasons, methods for coal desulfurization have been sought, which methods have employed mechanical, chemical and microbial means. These methods have involved intervention at different stages of the coal combustion process from scrubbing the coal prior to combustion (precombustion desulfurization) to removal of the sulfur oxides from the flue gas prior to discharge into the atmosphere (postcombustion desulfurization).

Efficient precombustion microbial desulfurization of coal offers many advantages over other methods of coal desulfurization. For example, precombustion microbial desulfurization requires relatively low capital investment and operating costs. It requires comparatively little energy as it does not require high temperatures or pressures to operate effectively. Microbial desulfurization is highly specific for removal of the offending sulfur compounds and results in little or no appreciable loss of valuable coal particles.

In order to maximize the efficiency of a system using microbial desulfurization, the reaction medium in such a system should be able to support high pulp densities of coal, preferably greater than 50 percent. Use of high pulp densities would allow larger masses of coal to be processed per unit of total reaction volume. However, effective removal of sulfur from high pulp densities requires a dense cell population of microorganisms in the reaction medium.

The electrolytic bioreactor assembly and method of the present invention are directed to the growth of dense populations of chemolithotrophic organisms. It should be noted that while the present invention particularly is useful for coal desulfurization, the dense innoculums of such organisms made possible by this invention also will have other uses, such as basic and applied research.

With reference to the figures generally, the electrolytic bioreactor of the present invention comprises a reaction vessel, designated generally by the numeral 10. The reaction vessel 10 defines a cultivation chamber 12 and an anode chamber 14. The cultivation chamber 12 is adapted for containing a culture solution and a cathode 16. The anode chamber 14 is adapted for containing an electrolyte solution and an anode 18, and is disposed in fluid communication with the cultivation chamber 12. The reaction vessel 10 is adapted for mounting a selective barrier 20 between the anode chamber 14 and the cultivation chamber 12 so that the selective barrier 20 will separate the anode chamber 14 from the cultivation chamber 12 but will allow fluid communication therebetween.

As shown in the figures generally, the reaction vessel 10 preferably is a cylinder. A cylindrical shape simplifies assembly, disassembly and cleaning of the vessel 10, and minimizes dead space in the cultivation chamber 12 while the culture solution is being stirred, as described more fully below.

The reaction vessel 10 preferably is constructed of a material which is non-toxic, machinable and compatible with mineral acids. Suitable materials include polycarbonates, Teflon, polyethylene, polypropylene and plexiglass. More preferably, Plexiglass R (Rohm & Haas) is utilized as it is transparent, available in a variety of tubing sizes (for cylindrical vessels) and plate sizes (for covers and floors of vessels), easy to machine, and relatively inexpensive.

In the preferred embodiment shown in the figures, the cultivation chamber 12 is substantially coextensive with the reaction vessel 10. The anode chamber 14 preferably then is a pocket-shaped space disposed adjacent to, and in face to face engagement with, a portion of the side wall 22 of the reaction vessel 10 so that the contour of the anode chamber 14 conforms to the contour of the side wall 22 of the reaction vessel 10.

The anode chamber 14 may be created by machining a window 24 into a portion of the side wall 22 of the reaction vessel 10 and overlaying the window 24 with a sheet of semi-permeable material to form the selective barrier 20. Next, a gasket 26, preferably of neoprene, and into which a window also has been cut, is placed over the selective barrier 20. Finally, a tubular section of material is placed over the gasket 26 to form the outer wall 28 of the anode chamber 14. Preferably, the outer wall 28 of the anode chamber 14 is composed of the same material as is the reaction vessel 10. The outer wall 28, gasket 26 and selective barrier 20 then are secured in a leakproof manner, such as by Teflon bolts 30, to the side wall 22 of the reaction vessel 10. Further, the outer wall 28, gasket 26 and bolts 30 assembly serve to mount the selective barrier 20 between the anode chamber 14 and the cultivation chamber 12 so that the selective barrier 20 will separate the anode chamber 14 from the cultivation chamber 12 but will allow fluid communication therebetween. Thus, the selective barrier 20, when mounted thusly, forms the inner wall of the anode chamber 14 and a portion of the side wall 22 of the reaction vessel 10.

The selective barrier 20 preferably is composed of a thin, flexible material conformable to the contour of the side wall 22 of the reaction vessel 10. As indicated above, the selective barrier 20 is formed of a material which is substantially impermeable to cations within the anode chamber 14 and to the organisms within the cultivation chamber 12. Because the selective barrier 20 is in direct contact with the organisms during cultivation, the selective barrier 20 also preferably is of a material which is non-toxic to the selected organisms. A preferred selective barrier 20 material is an anionic exchange membrane such as the membrane Type 204 SX ZL-386 available from Ionics, Inc.

Also as shown in the drawings generally, the anode chamber 14 is substantially smaller than the cultivation chamber 12 and has a capacity of about 0.5 percent to about 50 percent, and more preferably about 1 percent to 3 percent, of the capacity of the cultivation chamber 12. The volume of the anode chamber 14 preferably is no more than sufficient to immerse the anode 18, as described below, in liquid. The larger relative volume of the cultivation chamber 12 maximizes the space available within the reaction vessel 10 for growing organisms. Likewise, the relatively larger cultivation chamber permits efficient use of electric current in the system.

A bottom 32 and a cover plate 34, also preferably of the same material, may be machined to fit the reaction vessel 10. The bottom 32 preferably is permanently affixed to the reaction vessel 10 and suitably sealed to prevent fluid leakage. The cover plate 34 preferably is adapted to rest removably over the top of the reaction vessel 10. Preferably, a sample port 35 is constructed in the side wall 22 of the reaction vessel 10 near its top to allow the withdrawal of samples of culture solution from the cultivation chamber 12.

Figure 2:
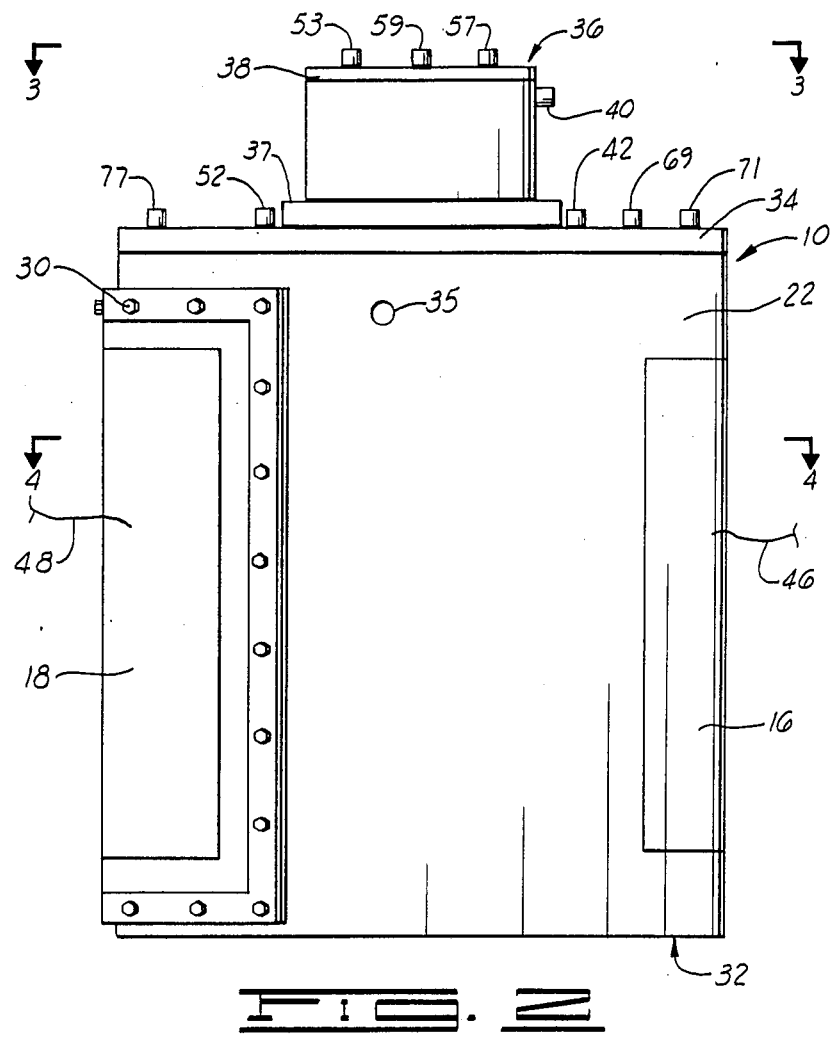
FIG. 2 is a side elevational view of the reaction vessel. In this embodiment a receptacle defining a pH control chamber is disposed immediately above the reaction vessel.

Referring to FIGS. 1 and 2, the electrolytic reactor of the present invention further comprises a receptacle 36 having a base 37 and a lid 38. The base 37 preferably is permanently affixed to the receptacle 36 and suitably sealed to prevent leakage. A square base is preferred as it will give added stability to the receptacle 36. The lid 38 preferably is adapted to rest securely but removably over the top of the receptacle 36.

The receptacle 36 defines a pH control chamber 39 which is adapted for receiving samples of the culture solution from the cultivation chamber 12. As shown semi-schematically in FIG. 1, the pH control chamber 39 is connectable by a conduit to the cultivation chamber 12 so that the solution samples within the pH control chamber 39 are insulated from electric current passing through the cultivation chamber 12. Preferably, the pH control chamber 39 is disposed immediately above the cultivation chamber 12. For example, it may be designed to rest upon the cover plate 34, as shown in FIG. 2. In the preferred embodiment and as shown in FIG. 1, the receptacle 36 is equipped with an overflow port 40 connectable by a conduit, such as flexible tubing, to a pH control chamber drainage port 42 in the cover plate 34 of the reaction vessel 10.

As depicted in the semi-schematic diagram of FIG. 1, the above-described bioreactor is adapted to be interfaced with systems for pH and temperature control, agitation, aeration and electrolysis of the culture solution within the cultivation chamber 12. The reactor and these systems comprise the electrolytic bioreactor assembly of the present invention.

Figure 4:
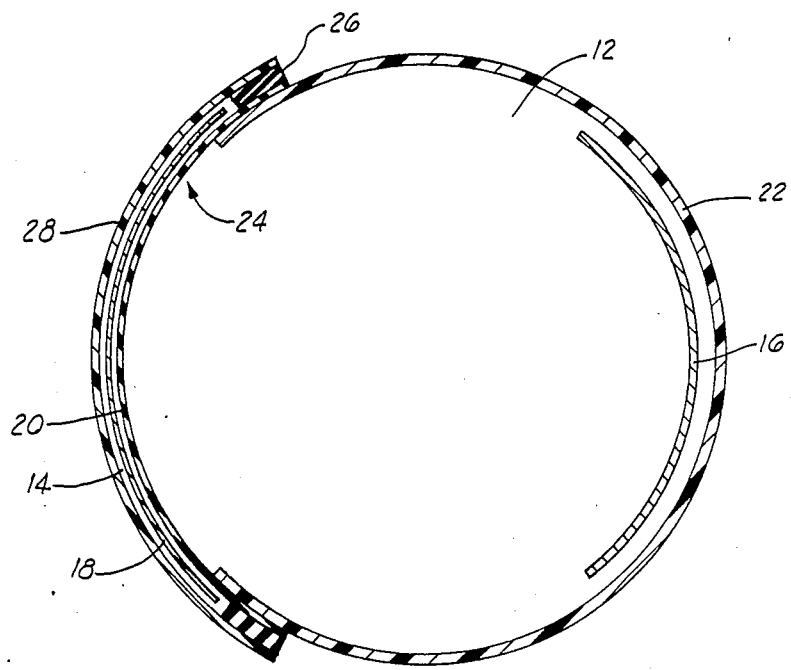
FIG. 4 is a cross-sectional view of the reaction vessel taken along line 4—4 of FIG. 2.
Figure 5:
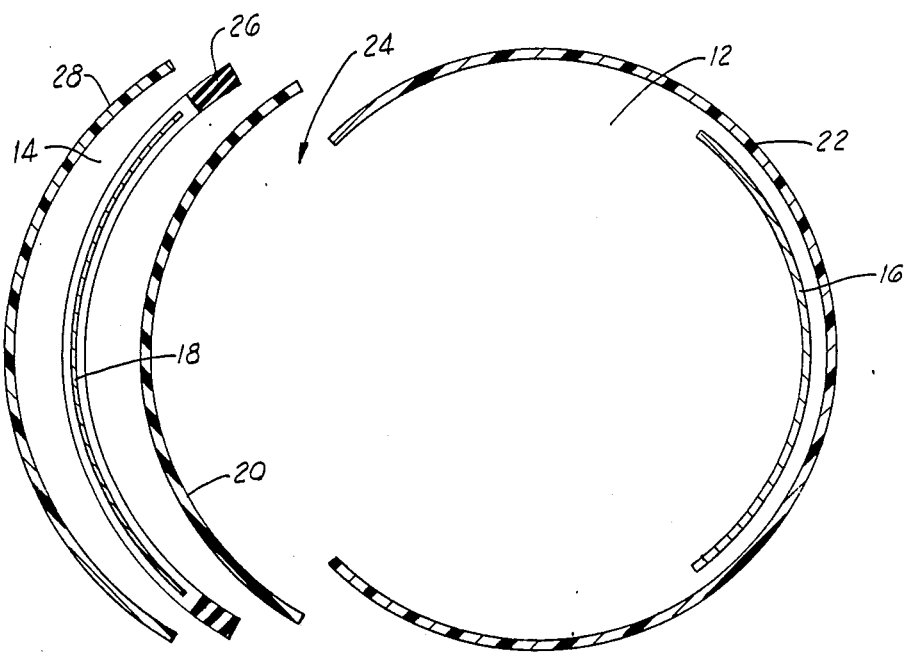
FIG. 5 is an exploded cross-sectional view of the reaction vessel taken along line 4—4 of FIG. 2.

Referring to FIGS. 4 and 5, in addition to the bioreactor described above, the electrolytic bioreactor assembly of the present invention further comprises a cathode 16 disposed within the cultivation chamber 12 and an anode 18 disposed within the anode chamber 14. Both electrodes preferably are composed of conductive material which is inert, non-toxic to the organisms to be grown, able to withstand mineral acid attack. Preferably, the electrode material is available in thin, flexible sheets to minimize electrode volume, to maximize available surface area and to be conformable to contours of the side wall 22 of the reaction vessel 10. A suitable electrode material is platinum.

The anode 18 preferably is shaped so as to fit comfortably within the pocket-shaped anode chamber 14 of the preferred embodiment. Thus, the anode 18 may be placed as a layer between the selective barrier 20 and the outer wall 28 and within the boundary formed by the windowed gasket 26. The anode chamber 14 then may be made water tight, preferably by securely bolting the layers—the outer wall 28, the gasket 26 and the selective barrier 20—to the vessel 10 around the window 24 with the Teflon bolts 30, as described above.

The cathode 16 preferably is of a size and shape about equivalent to the anode 18. Thereby, the cathode 16 may be placed within the cultivation chamber 12 of the reaction vessel 10 and preferably anchored to the inside of the side wall 22 in a position opposite to the window 24.

Figure 3:
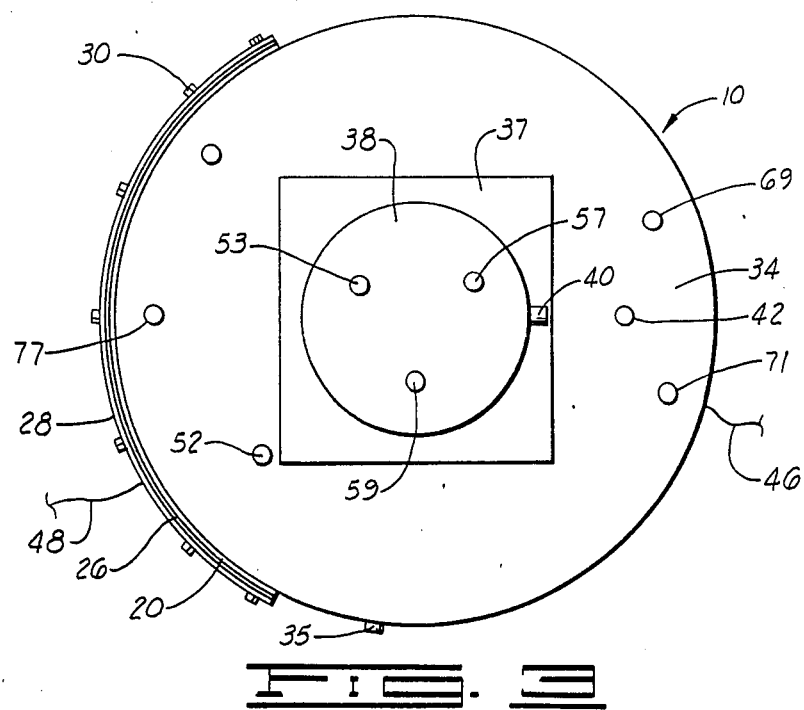
FIG. 3 is a plan view of the reaction vessel shown in FIG. 2.

As shown in FIG. 1, both the cathode 16 and the anode 18 are adapted to be connectable to a DC power supply 44 which functions to establish a potential difference between the cathode 16 and the anode 18. For example, as is shown in FIGS. 2 and 3, the ends of short pieces of platinum wires 46 and 48 may be welded to the center of the cathode 16 and the anode 18, respectively. The loose end of the wires 46 and 48 then may be inserted through small holes in the outer wall 28 of the anode chamber 14 and the side wall 22 of the reaction vessel 10 adjacent the cathode 16. The holes in the side wall 22 and the outer wall 28 then should be sealed in a suitable manner, such as by plugging around the wires 46 and 48 with a conformable coating. These electrode wires 46 and 48 then may be connected electrically to the DC power source 44, as shown schematically in FIG. 1.

The electrolytic bioreactor assembly of the present invention further comprises a pH maintenance system which functions to maintain the culture solution with the cultivation chamber 12 at a selected pH. With reference to FIG. 1, the pH maintenance system comprises a first peristaltic pump 50 connectable by a conduit, such as flexible tubing, to the cultivation chamber 12 and to the pH control chamber 39. Preferably, the aspirating or inlet end of the first pH pump tubing extends through a sample aspiration port 52 in the coverplate 34 well beneath the level of the culture solution within the cultivation chamber 12. The outlet end of the pH pump tubing enters the pH control chamber 39 through a sample entry port 53 in the lid 38 of the receptacle 36. The first pH pump 50 and tubing, in combination with the pH control chamber 39 overflow system, function to circulate samples of culture solution from the cultivation chamber 12 through the pH control chamber 39, so that the culture solution samples within the pH control chamber 39 are insulated from electric current within the cultivation chamber 12.

The pH maintenance system further comprises a pH controller 54 as shown in FIG. 1. The pH controller 54 preferably includes a pH probe 56 which is adapted to be inserted through a pH probe port 57 into the culture solution within the pH control chamber 39. Thus, the pH probe 56 and pH controller 54 function to monitor the pH of the culture solution within the pH control chamber 39.

With continuing reference to FIG. 1, the pH controller 54 also preferably comprises an acid reservoir 58, such as a 250 ml Erlenmeyer flask, which is connected to the pH control chamber 39 by a conduit, such as flexible tubing, to an acid inlet port 59 in the lid 38 of the receptacle 36. In line between the pH control chamber 39 and the acid reservoir 58 is a second peristaltic pump 60 capable of receiving and responding to signals from the pH controller 54. Specifically, the second peristaltic pump 60 acts to add acid from the acid reservoir 58 via the conduit to the culture solution in the pH control chamber 39 when the pH probe 56 registers a pH in the culture solution in the pH control chamber 39 which is below a selected value. Thus, the pH controller 54, with the second peristaltic pump 60 and the acid reservoir 58, function to adjust the pH of the culture solution with the pH control chamber 39 in response to the reading received by the pH controller 54 from the pH probe 56.

A suitable pH control system utilizes a low output pump having an adjustable stroke volume, such as the Cole Parmer Metering Pump, Series C-150 OSP, as the second peristaltic pump 60. The Cole Parmer Pump may be interfaced with an analog type pH controller, such as a Horizon Ecology Co. pH Controller, Type 5597, which has a sensitivity within about ±0.1 pH units.

Still referring to FIG. 1, the electrolytic bioreactor assembly of the present invention preferably also comprises an electrolyte reservoir 62, such as a ten liter carboy, adapted for containing a fresh electrolyte solution. The electrolyte reservoir 62 is disposed in fluid communication with the anode chamber 14, preferably by a conduit, such as tubing. Preferably the end of such conduit is connected to the bottom of the anode chamber 14. Preferably, the electrolyte reservoir 62 is positioned above the anode chamber 14 so that fresh electrolyte solution in the electrolyte reservoir 62 may be transferred by force of gravity through the conduit from the electrolyte reservoir 62 into the anode chamber 14.

The electrolytic bioreactor assembly of the present invention preferably also comprises an electrolyte catch tank 64, such as a ten liter carboy, adapted for receiving overflow electrolyte solution from the anode chamber 14. Preferably, the catch tank 64 is connected to the top of the anode chamber 14 by a conduit, such as tubing. Preferably, the electrolyte catch tank 64 is positioned below the anode chamber 14 so that overflow electrolyte solution from the anode chamber 14 may be transferred by force of gravity to the electrolyte catch tank 64. The conduits of the electrolyte reservoir 62 and the electrolyte catch tank 64 preferably are removably connected to the anode chamber 14, such by using a syringe needle on the end of the conduit, which needles may be inserted through the gasket 26 at the desired positions. Thus, the electrolyte reservoir 62 and electrolyte catch tank 64, with their respective conduits and connections to the anode chamber 14 function to continuously refresh the electrolyte solution within the anode chamber 14.

The electrolytic bioreactor assembly of the present invention preferably also comprises a temperature control system which functions to maintain the culture solution within the cultivation chamber 12 at a selected temperature. Preferably, the temperature control system comprises a temperature controller 66, as shown in FIG. 1. The temperature controller 66 preferably comprises a temperature probe 68 for sensing the temperature of the cultivation solution in the cultivation chamber 12. As shown in FIG. 1, the temperature probe 68 preferably is adapted for positioning in a temperature probe port 69 in the cover plate 34 so that the probe 68 may be partially immersed in the culture solution in the cultivation chamber 12. The temperature probe 68 also is connected electrically to the temperature controller 66 so that the temperature readings received by the probe 68 may be transmitted to the temperature controller 66.

The temperature controller 66 preferably also comprises a heating element 70 which also is connected electrically to the temperature controller 66. The heating element 70 is adapted for insertion through a heating element port 71 on the coverplate 34 so that the heating element 70 may be partially immersed into the culture solution within the cultivation chamber 12. In this way, the temperature controller 66 may regulate heat emitted by the heating element 70 in response to the temperature readings received from the temperature probe 68.

The electrolytic bioreactor assembly of the present invention preferably further comprises an aeration system for aerating the culture solution within the cultivation chamber 12. Preferably the aeration system is capable of introducing into the culture solution oxygen, which may be in the form of ambient air, and carbon dioxide gas. As shown in FIG. 1, the aeration system of the preferred embodiment of the present invention comprises a tank 72 of compressed carbon dioxide connected to a flow meter 74 for controlling and measuring the flow of gas from the carbon dioxide tank 72. Referring still to FIG. 1, the flow meter 74 also preferably is capable of mixing ambient air with the carbon dioxide in a selected ratio.

The carbon dioxide-air mixture then is transferred to the culture solution in the cultivation chamber 12 via a conduit, such as tubing, which connects the gas outlet of the flow meter 74 to the cultivation chamber 12. Preferably, the carbon dioxide-air mixture is released into the culture solution near the bottom 32 of the cultivation chamber 12 through a fitted glass disperser 76, so that the gas will bubble up through, and thereby aerate, the culture solution. Preferably, the disperser 76 is adapted to be positioned in a disperser port 77 located in the coverplate 34.

Referring to FIGS. 1, 4 and 5, the preferred embodiment of the bioreactor assembly of the present invention further comprises a stirring mechanism which functions to agitate the culture solution within the cultivation chamber 12. Preferably, the stirring mechanism comprises a stirring element 76 positioned on the bottom 32 of the cultivation chamber 12. A suitable stirring mechanism is a magnetic stir bar apparatus, comprising a stirring element 78, which may be positioned on the bottom of the reaction vessel 10 within the cultivation chamber 12, and a magnetic stirrer 80.

In accordance with the method of the present invention, the electrolytic bioreactor and assembly, described above, are used to grow chemolithotrophic organisms capable of oxidizing metal sulfides. The reactor assembly first is cleaned and primed.

With the sample port 35 plugged, the reaction vessel 10 is filled with about ten liters of a suitable cleaning solution, such as a sulfuric acid solution, having a pH of about 1.0. The cleaning solution then is agitated, such as by the stir bar apparatus for about 12 hours. This agitation period allows residual compound (ferric hydroxides, other salts or oxidized mineral forms) to be leached out of the selective barrier 20 and the inner surfaces of the reaction vessel 10. Following the agitation period, the reaction vessel 10 is drained and filled with about ten liters of deionized water. The stirring element 78 preferably is left in place on the bottom 32 of the reaction vessel 10.

All conduits (except the gas conduit from the aeration system) between the reaction vessel 10 and the systems interfaced with the reaction vessel 10 are flushed with the cleaning solution. Following such flushing, the conduits are primed by filling them with deionized water.

The anode chamber 14 also preferably is flushed with the cleaning solution. After flushing with both inlet and outlet ports closed, the anode chamber then is primed by filling with an acid solution, such as sulfuric acid. The pH of the primary solution preferably is about 1.6.

The elements of the temperature control system and the pH control system are cleaned and prepared in a manner consistent with the manufacturer's instructions. For example, the temperature probe 68 and heating element 70 may be cleaned with the acidic (pH 1.0) cleaning solution and allowed to air dry. The electrolyte solution in the pH prober 56 preferably is replaced with fresh solution and the outside of the pH prober 56 may be rinsed with acidic cleaning solution and immersed in a buffer solution (pH 2.0) until ready for use.

The gas disperser 76 preferably also is cleaned, such as by soaking in a 1N solution of sulfuric acid (1N $H_2SO_4$), to dissolve any ferric precipitates. The disperser 76 then may be stored in deionized water.

The electrolyte reservoir 62 preferably is drained and washed with a suitable cleaning solution. For example, the ten liter carboy used in the preferred embodiment of the present invention may be washed with a 10N sulfuric acid solution and then rinsed with an acid cleaning solution, such as sulfuric acid (pH 1.0). The cleaned electrolyte reservoir 62 preferably is primed with deionized water, the pH of which then is adjusted with concentrated sulfuric acid to a pH of about 1.6.

After the reaction vessel 10 and the elements of the assembly have been cleaned and primed, the bioreactor assembly is assembled. The stirring mechanism is actuated and set at a stir rate sufficient to maintain the adequate agitation and assist in aeration. Where a stir bar apparatus is utilized, as in the preferred embodiment here, the magnetic stirrer is set at about 4.5.

The deionized water in the vessel 10 next is adjusted to constitute a culture solution comprising metal sulfide substrate. First, the pH of the water is reduced to about 1.6, preferably by adding concentrated sulfuric acid. Next a nutrient medium is added. A preferred nutrient medium is a modified Denisor's medium comprising (in grams per liter): $FeSO_4 \times 7H_2O$, 7.5; $(NH_4)_2SO_4$, 3.1; $KH_2PO_4$, 0.13; $H_3PO_4$, 0.18 (0.10 mls); $MgSO_4 \times 7H_2O$, 0.15. The respective amounts of the nutrients preferably are added to ten liters of deionized water in the cultivation chamber 12.

The gas disperser 76 is inserted through the disperser port 77 in the coverplate 34 which then is placed over the top of the reaction vessel 10. Preferably, the coverplate 34 is positioned (rotated) so that the gas disperser 76 is nearest the anode chamber 14 and across from the cathode 16 so as to minimize the physical stress of the gas bubbles on the cathode 16. Tubing is attached to form a gas conduit from the mixing flow meter 74 to the gas disperser 76. The main valve on the carbon dioxide tank 72 is fully opened, the regulator on the flow meter 74 preferably is set to about 20 psig, and the valve on the carbon dioxide tank 72 gradually adjusted until the flow meter reads 1 c.f.h. Preferably, the mixer-flow meter 74 set to deliver twelve c.f.h. of room air with every one c.f.h. of carbon dioxide so that gas is discharged into the culture solution at a rate of 13 c.f.h.

Preferably, the pH control system next is assembled. The receptacle 36 first is positioned preferably on the center of the coverplate 34. Flexible tubing is attached to form a conduit from the overflow port 40 of the pH control chamber 38 to the pH drainage port 42 in the coverplate 34. The receptacle lid 38 next preferably is positioned over the mouth of the receptacle 36. Tubing is attached to form a conduit between the first peristaltic pump 50 and the sample entry port 53 in the lid 38 of the receptacle 36. Tubing is attached to form a conduit between the first peristaltic pump 50 and the cultivation chamber 12. The aspirating end 52 of the tubing is inserted through the sample aspiration port 52 in the coverplate 34 and positioned near the bottom 32 of the cultivation chamber 12. Tubing next is attached to form a conduit from the acid reservoir 58 through the second peristaltic pump 60 of the pH controller 54 and then to the acid inlet port 59 in the receptacle lid 38. The acid reservoir 58 next is substantially filled with an acid solution, preferably a 1:2 dilution of concentrated sulfuric acid and the end of the conduit (tubing) is immersed well into the acid solution.

Next, the first peristaltic pump 50 is turned on to a setting of 1 and the pH control chamber 39 is allowed to fill to overflowing. The overflow culture solution from the pH control chamber 39 then is allowed to drain through the overflow conduit back into the cultivation chamber 12. Once the volume of culture solution samples within the pH control chamber 39 has reached the overflow level, the pH probe 56 preferably is rinsed with deionized water and placed in the culture solution in the pH control chamber 39 by insertion through the pH probe port 57. The pH controller 54 next preferably is activated in the automatic mode and the limiter set to the selected pH, which preferably is about 1.7 when the selected organism is Thiobacillus ferrooxidans. The second peristaltic pump 60 is set to deliver into the pH control chamber 39 at a selected stroke volume of acid solution from the acid reservoir 58. A preferred acid stroke volume is 0.3 ml.

Preferably, next the temperature system is assembled. The temperature probe 68 from the temperature controller 66 is inserted through the temperature probe port 69 in the coverplate 34 and immersed partially in the culture solution. The heating element 70 from the temperature controller 66 preferably next is inserted through the heating element port 71 in the coverplate 34 and immersed in the culture solution in the cultivation chamber 12. The temperature controller 66 then preferably is set at the selected temperature. The gain then is set at about 50 percent and the culture solution in the cultivation chamber 12 is allowed to reach the selected operating temperature. The preferred operating temperature preferably is from about 25° C. to about 35° C., depending on the mineral sulfide oxidized and the strain of organisms to be grown. For example, the organism *Thiobacillus ferrooxidans* demonstrates optimal growth at 29° C.

Once the reactor assembly has been assembled and culture solution prepared and allowed to equilibrate at the selected pH and temperature, the selected organisms are contacted with the culture solution in the cultivation chamber 12. Preferably, a 25 ml aliquot of a concentrated innoculum of the selected chemolithotrophic organism, such as *Thiobacillus ferrooxidans*, is added to the prepared culture solution.

Once the organisms have been added to the culture solution in the cultivation chamber 12, the culture solution and the organisms are electrolyzed. The electrodes are electrically connected to the DC power source 44, such as by alligator clips. The internal ground option preferably is used for current referencing, since this prevents grounding through the pH probe 56. The negative terminal of the power source 44 is connected to the anode 18 and the positive terminal to the cathode 14. The power source 44 then is activated and set to deliver a constant applied current preferably of from about 250 mA to about 1000 mA, and more preferably at about 500 mA (3.85 volts).

The organisms having been contacted with the prepared culture solution in the cultivation chamber 12 of the reaction vessel 10 and the electrolysis being under way, the above described pH control system operates to maintain the culture solution during such growth and electrolysis at the selected pH. The first peristaltic pump 50 so functions to circulate samples of the culture solution through the pH control chamber 39 so that such samples are insulated therein from electric current within the cultivation chamber 12. The pH controller 54, with its pH probe 56, second peristaltic pump 60 and acid reservoir 58, serve to monitor the pH of the culture solution sample in the pH control chamber 39 and adjust the pH of such sample in response to such monitoring.

Preferably during electrolysis, the electrolyte solution in the anode chamber 14 is refreshed. The electrolyte reservoir 62, such as the ten liter carboy of the preferred embodiment, is substantially filled with electrolyte solution comprising about 18 mls of concentrated sulfuric acid in about 10 liters deionized water and having a pH about equal to the selected pH of the culture solution. The electrolyte reservoir 62 then may be positioned in a suitable manner above the level of fluid in the anode chamber 14. The electrolyte catch tank 64, such as the ten liter carboy of the preferred embodiment, is positioned below the level of fluid in the anode chamber 14. The conduits of the electrolyte reservoir 62 and the catch tank 64 are connected to the anode chamber 14 as described above, and the relative distance of each from the anode chamber 14 drains continuously into the catch tank 64 at a desired rate, while the electrolyte solution from the electrolyte reservoir 62 also continually is refilling the anode chamber 14 at a corresponding rate. The electrolyte reservoir 62 may be refilled and the catch tank 64 emptied as necessary during the course of electrolysis.

The temperature control system described above preferably is used to maintain the culture solution within the cultivation chamber 12 at a selected temperature. A preferred operating temperature of the culture solution is selected according to the organism to be grown.

Preferably, the aeration system described above serves to aerate the culture solution within the cultivation chamber 12 during electrolysis. The stirring mechanism, also described above, functions to agitate the culture solution within the cultivation chamber 12 during electrolysis. It should be noted that the stirring mechanism also acts to assist in aeration of the culture solution by causing the gas bubbles to be dispersed more evenly throughout the cultivation chamber 12.

During electrolysis, samples of the culture solution may be withdrawn, such as by a syringe, through the culture solution sample port 35. Such samples may be used, for example, to monitor ferrous iron concentration and protein content of the culture solution. Prior to withdrawal of such sample, it is preferred to replenish any volume lost through evaporation by refilling the cultivation chamber 12 to a pre-marked fill line with deionized water. The fill line preferably is determined in the absence of aeration and stirring.

The electrolytic bioreactor assembly is operated continuously until the growth of the organisms slows substantially. As described below, growth of the organisms may be determined by measuring protein concentration of the regularly drawn samples of the culture solution. When graphed, these measurements will reflect an eventual growth plateau, at which time the organisms may be collected and the run terminated.

EXAMPLES

Selection of Organism

Organisms which are chemolithotrophic bacteria capable of oxidizing ferrous ions ($Fe^{++}$) include *Sulfolobus acidocoldarius, Sulfobacillus thermosulfidooxidans, Sulfolobus acidophilus, Leptospirillum ferrooxidans,* Metallogenium sp., *Gallionella ferruginea,* and *Thiobacillus ferrooxidans. T. ferrooxidans* was selected for use in studying the present invention. This organism is an acidiphilic chemolithotrophic bacteria and can oxidize both reduced iron and sulfur compounds.

Culture Maintenance and Innoculum Preparation

The culture of *T. ferrooxidans* used in the present studies was isolated from a copper leach dump effluent stream sample supplied by Kennecott Corp., Santa Rita, N. Mex. A pure culture was isolated from a streak plate using silica gel plates which were impregnated with modified Denisov's culture solution (pH 1.6). This culture solution comprised (gr/l): $FeSO_4 \times 7H_2O$, 7.5; $(NH_4)_2SO_4$, 3.1; $KH_2PO_4$, 0.13; $H_3PO_4$, 0.18 (0.10 mls.); $MgSO_4 \times 7H_2O$, 0.15 and was adjusted to a pH of 1.6. The active cultures were maintained in 100 ml of modified Denisov's culture solution in 250 ml Erlenmeyer shaker flasks and agitated on a rotary shaker at 25° C. Innoculum for reactor runs was obtained by using a 4 liter Erlenmeyer flask containing 4 liters of culture solution. The flask was agitated using a teflon stir bar and a magnetic stir plate (Fisher 14-493-120T). Forced aeration was provided through laboratory pressurized air, which was introduced into the culture solution through a porous glass disperser at a rate of 13 c.f.h. In order to obtain a high recovery of the cells in the spent broth, any ferric ions/precipitates were first removed using Dowex cationic exchange beads (BioRad 50W-X8, 20–50 mesh). The cells were recovered by continuous centrifugation using a motor driven Sharples Super-Centrifuge. The concentrated cell mass was recovered in a volume of 300 ml, and further concentrated by filtration with a low vacuum source and a Pyrex filter holder, using 47 mm Durapore filters (Millipore HVLP 04700). 50 ml aliquots of the concentrated broth were impinged onto the filter. The filter then was removed from the holder and placed in a test tube with fresh culture solution (less the ferrous salt). The test tube was vortexed and the filter removed. This procedure was repeated until the cells were concentrated into 25 ml of culture solution. This was used to inoculate 10 liters of culture solution for a reactor run. The innoculum was prepared just prior to its use in a reactor run due to the rapid loss of activity when stored in a concentrated form. Innoculum was grown up in the reactor when adaptation to electrolysis was desired. The same procedure was used for concentration of the innoculum.

Ferrous Iron Assay Procedure

The present studies required repeated assessment of the ferrous iron content of the culture solution in the cultivation chamber of the bioreactor assembly. This determination was made using a standard colorimetric technique which utilizes the chromophore, 1, 10 phenanthroline. To 4.0 ml of 0.5 M HCl-KCl pH 2.0 buffer (Fischer Scientific Co. SO-B-96), 0.5 ml of a 0.25% 1, 10 phenanthroline solution was added. The culture solution sample was diluted so that the limits of resolution of the assay were not exceeded. To the phenanthroline/buffer solution, 0.5 ml of the appropriately diluted ferrous iron-containing sample was added. This mixture was vortexed and allowed to stand at room temperature for 1 hour. The solution was read spectrophotometrically at 500 nm on a Bausch & Lomb Spectronic 20, using deionized water as a standard. A standard curve was constructed using sulfuric acid solutions containing various amounts of ferrous sulphate heptahydrate. For determination of ferrous iron levels in the culture solution, the sample of culture solution was prefiltered to remove any bacterial cells and ferric precipitates. The sample then was diluted so as to make the concentration of the sample within the analytical range of the assay. The initial dilution was always known for any one reactor run since the composition of the culture solution was defined. Subsequent dilutions had to be determined based on the rate at which the iron was being oxidized.

Protein Concentration Assessment Procedure

The present studies required assessment of the growth rate of the organisms in the culture solution. For this purpose, protein production rate was assumed to be analogous to the specific growth rate of the organism. Accordingly, repeated assessment of protein concentration in the culture solution was performed.

The protein concentration in culture solution was determined using a modified Lowry technique (Kuriki and Racker, 1976 and Lowry, et al., 1957). A reagent composed of 50 parts of a 2.0% w/v solution of $Na_2CO_3$ monohydrate in 0.1N NaOH, 1 part of a 0.5% w/v solution $CuSO_4$ pentahydrate and 1 part of a 1.0% Na-K-Tartrate solution was prepared prior to the assay. The culture solution samples for protein assay were suspended in 0.5 ml of a 10% solution w/v Na-deoxycholate in NaOH (pH 11.6), vigorously vortexed and allowed to stand at 37° C. for 15 minutes. A 0.1 ml aliquot of the protein/deoxycholate solution was then introduced into the reagent mixture and vortexed. This was incubated at 37° C for 15 minutes. To this solution was added 0.1 ml of a 1:1 dilution of Folin and Ciocalteau Phenol Reagent; the final solution was vortexed and incubated for 15 minutes at 37° C. The resulting solution was filtered through a 13 mm Millipore (45 micron HVLP01300), using a syringe and a swinnex adapter. The filtered solution then was read spectrophotometrically at 750 nm using a Hitachi Digital Spectrophotometer (Model 191) using deionized water as a reference. A standard curve was constructed using bovine albumin as a standard. To determine the protein concentration in the culture solution, a 5-30 ml sample of the culture solution was filtered through a 13 mm Nucleopore filter (45 micron #110407) using a syringe and a swinnex adapter. The filter and the swinnex's internal rubber gasket were then transferred to 0.5 ml of the Na-deoxycholate solution. This solution then was processed as outlined above.

The quantity of culture solution to be filtered in order to obtain protein concentrations within the range of the assay was found to be related to the backpressure experienced during the filtration step. If a low pressure was encountered, more sample was filtered. The critical pressure indicative of an adequate sample was subjectively determined by repeated use of the assay. This technique of using filtration allowed for the determination of culture solution protein concentrations which were reflective of viable cells only. Disrupted cells would not be retained by the filter and thus would not be accounted for in the protein assay. The rubber gasket was included in the deoxycholate digestion due to its close association with the filter and, thus, potential site of cell attachment. It also served as a source of mechanical abrasion during the vortexing of the deoxycholate solution, thus aiding in the dissociation of cell from the membrane filter. All steps which involved contact with viable cells were carried out with either polycarbonate or polyethylene labware. This reduced the loss of cells due to their adsorption to glass.

Determination of Protein and Ferrous Iron Concentration Equations

To demonstrate the linear relationship between spectrophotometric measurement of the culture solution and the concentrations of protein and ferrous iron, the absorbency of a series of solutions having increasing concentrations were measured. The data from the ferrous iron assay standardization measurements is shown in Table 1. The spectrophotometric assay proved to be applicable for ferrous iron concentrations in the range of 0 ppm to 60 ppm. This data was plotted in a linear regression graph which disclosed a high coefficient of correlation for this assay of 0.999.

TABLE 1

| Ferrous Iron Assay Standardization Data* | | |
|---|---|---|
| Sample No. | Ferrous Iron Concentration (ppm) | Absorbance at 500 nm |
| 1 | 70 | 1.387 |
| 2 | 60 | 1.208 |
| 3 | 50 | 1.107 |
| 4 | 45 | 0.988 |
| 5 | 40 | 0.895 |
| 6 | 35 | 0.775 |
| 7 | 25 | 0.559 |
| 8 | 15 | 0.346 |
| 9 | 5 | 0.106 |

*Beer's law obeyed up to 100 mg/l.

Analysis of slopes and intercepts of the regression line led to the following equation for use in determining ferrous iron concentration in culture solution samples:

$$\text{ppm of } Fe^{+2} = 45.253 * (ABS_{500}) - 0.032f$$

The data from the protein assay standardization measurements, shown in Table 2, was similarly analyzed. This analysis showed a correlation coefficient of 0.9981 and that the protein assay was applicable for concentrations between 10-110 micrograms of protein per 0.1 ml sample. The following equation for measuring protein concentration in culture solution samples was formulated:

$$\text{micrograms of protein} = 121.727 * (ABS_{750}) - 11.25165$$

TABLE 2

| Protein Assay Standardization Data* | | |
|---|---|---|
| Sample No. | Protein (micrograms) | Absorbance (750 nm) |
| 1 | 100 | 0.9245 |
| 2 | 80 | 0.7258 |
| 3 | 60 | 0.6615 |
| 4 | 40 | 0.4280 |
| 5 | 30 | 0.3655 |
| 6 | 25 | 0.2920 |
| 7 | 20 | 0.2676 |
| 8 | 15 | 0.2069 |
| 9 | 10 | 0.1580 |

*Beer's law obeyed up to 50 ppm.

Determination of Equation for Microbial Ferrous Iron Oxidation Rate

To determine an equation for measuring microbial oxidation of ferrous iron, five reactor runs were performed according to the procedures described above. The data from these runs are set out in Table 3. As indicated in the table, the linear regression equation and coefficient of correlation was determined for each of the five runs. The slope of the regression line for each run was plotted against its respective amperages yielding a coefficient of correlation of 0.9882. The slope and intercept of this regression line then was used to formulate the following equation which defines the relationship between applied current and ferrous iron production rate:

$$(dFe^{+2}/dt) = I * 0.124$$

where $dFe^{+2}/dt$ = mg ferrous iron/1 hr., and I = milliamps.

The above equation then was used to formulate an equation for measuring the microbial ferrous iron oxidation for a selected time interval of a reactor run. For a specified time interval ($t_F - t_X$), the microbial ferrous iron oxidation rate is:

$$(dFe^{+2}/dt)_M = (dFe^{+2}/dt)_T - (dFe^{+2}/dt)_E$$

where M, T and E stand for microbial, total and electrolytic, respectively.

The quantity of ferrous iron oxidized microbially was determined by the following equation:

$$(dFe^{+2}/dt)_M = \frac{(Fe_X - Fe_E) + (dFe^{+2}/dt) \times (t_F - t_E)}{(t_F - t_X)}$$

where
$Fe_X$ = ferrous iron concentration (in mg/l) at the beginning of the time interval;
$Fe_F$ = ferrous iron concentration (in mg/l) at the end of the time interval;
$t_X$ = initial time (hour);
$t_F$ = final time (hour);
$t_E$ = time at which electrolysis was initial electrolysis (hour)

It should be noted that the fourth run extended over a period of nearly three hours, whereas the other four runs involved periods of about 1 hour. As the data shows, this long run had a coefficient of correlation comparable to the other runs. This indicated that the ferrous iron production rate remained constant over prolonged current applications.

It also should be noted that the fifth run was conducted at a temperature of 24° C. whereas the other four runs were conducted at 29° C. This run was conducted to determine if the ferrous iron production rate was temperature related. From the data obtained, it was concluded that for the temperature range measured, the ferrous iron production rate was the same across the temperature range at a constant amperage of 500 mA.

TABLE 3
Effect of Applied Current on Ferrous Production*

| Set No. | Temp. | Milliamps | Hours | ABS(dilution) | ppm $Fe_{+2}$ |
|---|---|---|---|---|---|
| 1 | 29 C. | 1000 | 0 | 0.942/— | 4.231 |
| | " | | 0.5 | 1.222/— | 55.26 |
| | " | | 0.75 | 0.118/(1/20) | 106.2 |
| | " | | 1.00 | 0.147/(1/20) | 131.2 |
| | " | | 1.25 | 0.181/(1/20) | 163.3 |
| | " | | 1.50 | 0.208/(1/20) | 187.2 |

Coefficient of correlation: 0.995
Linear regression equation: ppm $Fe_{+2}$ = 126.11 (hours) + 2.806

| 2 | 29 C. | 750 | 0 | 0.244/(1/20) | 220.3 |
|---|---|---|---|---|---|
| | " | | 0.2 | 0.276/(1/20) | 248.9 |
| | " | | 0.45 | 0.303/(1/20) | 273.4 |
| | " | | 0.70 | 0.322/(1/20) | 290.3 |

Coefficient of correlation: 0.987
Linear regression equation: PPM $Fe_{+2}$ = 99.03 (hours) + 195.07

| 3 | 29 C. | 500 | 0 | 0.248/(1/20) | 223.7 |
|---|---|---|---|---|---|
| | " | | 0.30 | 0.277/(1/20) | 250.4 |
| | " | | 0.517 | 0.301/(1/20) | 271.8 |
| | " | | 0.75 | 0.317/(1/20) | 286.2 |
| | " | | 1.0 | 0.347/(1/20) | 313.2 |

Coefficient of correlation: 0.998
Linear regression equation: PPM $Fe_{+2}$ = 87.71 (hours) + 224.02

| 4 | 29 C. | 250 | 0 | 0.290/(1/20) | 261.7 |
|---|---|---|---|---|---|
| | " | | 0.25 | 0.311/(1/20) | 280.5 |
| | " | | 0.416 | 0.314/(1/20) | 283.8 |
| | " | | 2.467 | 0.421/(1/20) | 380.7 |
| | " | | 2.80 | 0.450/(1/20) | 406.4 |

Coefficient of correlation: 0.998
Linear regression equation: ppm $Fe_{+2}$ = 49.32 (hours) + 264.1

| 5 | 24 C. | 500 | 0 | 0.415/(1/20) | 374.5 |
|---|---|---|---|---|---|
| | " | | 0.3 | 0.427/(1/20) | 385.9 |
| | " | | 0.55 | 0.451/(1/20) | 407.5 |
| | " | | 0.766 | 0.480/(1/20) | 433.9 |
| | " | | 1.05 | 0.503/(1/20) | 453.7 |

Coefficient of correlation: 0.986
Linear regression equation: ppm $Fe_{+2}$ = 79.69 (hours) + 368.62

*Each of the runs was conducted using a pH of 1.7, aeration at the rate of 13 c.f.h. with a $CO_2$–air ratio of 12:1, and a modified Denisov's medium with ferric sulfate as culture solution.

Growth Studies

Having formulated equations for calculating the critical parameters—namely, protein (cell) concentration, ferrous iron concentration, protein production rate, iron oxidation rate, and yield coefficient (cellular metabolic efficiency), studies were performed to determine the efficiency of the present invention for growing chemolithotrophic organisms. Also, studies were conducted to determine the optimum temperature and current amperage for growing T. ferrooxidans, specifically.

Six reactor runs were conducted. In each run, the pH of the culture solution was maintained at 1.7, aeration of carbon dioxide and air was maintained in a ratio of 1:12 for a total flow of 13 c.f.h. Except for temperature and current, the run procedure otherwise was conducted in accordance with the method described above and using a bioreactor assembly of the design described above. Each of the six runs was conducted at a constant temperature over a time period ranging from about 27 hours to about 89 hours. The data from these reactor runs is set out in Tables 4 through 9.

The first part of each run was conducted without electrolysis. The data of this initial (pre-electrolysis) part of each run generally demonstrates a typical growth pattern for these microorganisms: a beginning lag phase, a logarithmic (growth) phase and a stationary phase.

TABLE 4
Reactor Run Data at Temperature of 24° C.

| Time in Hours | Applied Current (milliamps) | $ABS_{500}$/dil. | $ABS_{750}$/ sample | $Fe^{++}$ (ppm) | Protein (mg/l) |
|---|---|---|---|---|---|
| 0.00 | — | 0.6271/(1/50) | 0.1818/10 ml | 1417.3 | 5.438 |
| 4.00 | — | 0.4854/(1/50) | 0.1630/10 ml | 1096.8 | 4.298 |
| 8.00 | — | 0.3468/(1/50) | 0.1675/10 ml | 783.0 | 4.568 |
| 14.25 | — | 0.2240/(1/50) | 0.1695/10 ml | 505.26 | 4.681 |
| 16.75 | — | 0.2716/(1/35) | 0.1904/10 ml | 429.10 | 5.965 |
| 20.75 | — | 0.4067/(1/15) | 0.2097/10 ml | 275.58 | 7.138 |
| 24.75 | — | 0.2708/(1/15) | 0.2652/10 ml | 183.35 | 10.515 |
| 29.00 | — | 0.2480/(1/15) | 0.2526/10 ml | 111.88 | 9.748 |
| 30.50 | 250 | | | | |
| 32.75 | 250 | 0.3288/(1/10) | 0.2652/10 ml | 148.48 | 10.515 |
| 33.75 | 500 | | | | |
| 36.75 | " | 0.6968/(1/10 | 0.1824/5 ml | 315.00 | 10.956 |
| 39.00 | " | 0.8539/(1/20) | 0.1838/5 ml | 386.58 | 11.117 |
| 40.75 | " | 0.4815/(1/20) | 0.1904/5 ml | 429.25 | 11.930 |
| 44.75 | " | 0.4750/(1/20) | 0.2154/5 ml | 435.12 | 14.966 |
| 49.25 | " | 0.4815/(1/20) | 0.2388/5 ml | 435.12 | 17.820 |
| 52.50 | " | 0.2549/(1/30) | 0.2541/5 ml | 345.00 | 19.684 |
| 54.50 | " | 0.3487/(1/20) | 0.2596/5 ml | 315.96 | 20.353 |
| 56.00 | " | 0.1713/(1/20 | 0.2620/5 ml | 231.63 | 20.642 |
| 57.00 | 800 | | | | |
| 64.50 | 800 | 0.1198/(1/20) | 0.2692/5 ml | 107.73 | 21.519 |
| 64.75 | 1200 | | | | |
| 69.25 | 1200 | 0.1192/(1/15) | 0.2204/5 ml | 80.42 | 15.577 |

TABLE 5
Reactor Run Data at Temperature of 26° C.

| Time in Hours | Applied Current (milliamps) | $ABS_{500}$/dil. | $ABS_{750}$/ sample | $Fe^{++}$ (ppm) | Protein (mg/l) |
|---|---|---|---|---|---|
| 0.00 | — | 0.6726/(1/50) | 0.07186/20 ml | 1452.3 | 0.4974 |
| 5.00 | — | 0.6964/(1/50) | 0.0915/20 ml | 1310.9 | 0.6606 |
| 17.00 | — | 0.4160/(1/50) | 0.1325/15 ml | 904.3 | 2.027 |
| 24.00 | — | 0.1649/(1/50) | 0.2136/15 ml | 368.4 | 4.029 |
| 30.00 | — | 0.4089/— | 0.1739/10 ml | 17.79 | 4.776 |
| 31.00 | 500 | | | | |
| 38.00 | " | 0.4437/— | 0.2366/10 ml | 19.27 | 7.402 |
| 43.00 | " | 1.2290/— | 0.1972/7 ml | 52.81 | 8.217 |
| 48.00 | " | 0.2110/(1/10) | 0.2848/7 ml | 93.40 | 13.47 |
| 53.00 | " | 0.1800/(1/10) | 0.3089/7 ml | 80.11 | 14.91 |
| 54.00 | 750 | | | | |
| 59.00 | " | 0.1520/(1/10) | 0.2907/5 ml | 68.07 | 19.35 |
| 65.50 | " | 0.0890/(1/20) | 0.3363/5 ml | 82.38 | 23.17 |
| 66.50 | 1000 | | | | |
| 76.50 | " | 0.0850/— | 0.2933/5.3 ml | 3.54 | 23.50 |
| 88.50 | " | 0.0870/— | 0.3958/5.8 ml | 4.03 | 24.27 |

TABLE 6

Reactor Run Data at Temperature of 29° C.

| Time in Hours | Applied Current (milliamps) | $ABS_{500}$/dil. | $ABS_{750}$/sample | $Fe^{++}$ (ppm) | Protein (mg/l) |
|---|---|---|---|---|---|
| 0.00 | — | 0.6556/(1/50) | 0.2620/10 ml | 1481.78 | 10.321 |
| 2.75 | — | 0.4271/(1/50) | 0.2933/10 ml | 964.80 | 12.328 |
| 6.00 | — | 0.3233/(1/20) | 0.1938/5 ml | 291.96 | 12.341 |
| 7.10 | 550 | | | | |
| 8.75 | " | 0.1797/(1/20) | 0.2118/5 ml | 162.07 | 14.533 |
| 12.00 | " | 0.2899/(1/10) | 0.2306/5 ml | 130.85 | 16.821 |
| 15.00 | " | 0.1915/(1/10) | 0.2388/5 ml | 131.62 | 17.817 |
| 15.25 | 800 | | | | |
| 19.00 | " | 0.3487/(1/10) | 0.2396/5 ml | 157.48 | 17.911 |
| 24.25 | " | 0.3925/(1/10) | 0.3170/5 ml | 177.31 | 27.330 |
| 27.00 | " | 0.3726/(1/10) | 0.3224/5 ml | 168.30 | 27.991 |
| 27.75 | 1000 | | | | |
| 29.50 | " | 0.3334/(1/10) | 0.3665/5 ml | 150.58 | 33.365 |
| 30.75 | " | 0.3458/(1/10) | 0.3297/5 ml | 156.17 | 28.883 |
| 33.75 | " | 0.3089/(1/10) | 0.2873/5 ml | 139.47 | 23.727 |

TABLE 7

Reactor Run Data at Temperature of 29° C. and Using Innoculum of Organisms Cultured under Electrolysis (pre-adopted)

| Time in Hours | Applied Current (milliamps) | $ABS_{500}$/dil. | $ABS_{750}$/sample | $Fe^{++}$ (ppm) | Protein (mg/l) |
|---|---|---|---|---|---|
| 0.00 | — | 0.6536/(1/50) | 0.1868/15 ml | 1477.1 | 3.7865 |
| 3.50 | — | 0.5072/(1/50) | 0.5072/10 ml | 1146.1 | 5.1180 |
| 7.00 | — | 0.3883/(1/50) | 0.1904/10 ml | 876.90 | 5.965 |
| 11.00 | — | 0.5214/(1/25) | 0.2190/10 ml | 589.09 | 7.701 |
| 16.00 | — | 0.2926/(1/20) | 0.2062/10 ml | 264.00 | 6.925 |
| 17.30 | 250 | | | | |
| 19.50 | 250 | 0.3019/(1/20) | 0.2472/10 ml | 272.58 | 9.119 |
| 23.50 | 250 | 0.3363/(1/20) | 0.2874/10 ml | 303.72 | 11.863 |
| 27.25 | 250 | 0.3458/(1/20) | 0.2790/10 ml | 312.34 | 11.356 |
| 29.42 | 500 | | | | |
| 32.00 | 500 | 0.4581/(1/20) | 0.2549/7 ml | 414.24 | 14.128 |
| 36.00 | 500 | 0.5817/(1/20) | 0.1925/5 ml | 525.82 | 12.176 |
| 38.00 | 750 | | | | |
| 40.50 | 750 | 0.4935/(1/20) | 0.2306/5 ml | 445.99 | 16.820 |
| 45.50 | 750 | 0.4342/(1/20) | 0.1972/5 ml | 392.28 | 12.756 |
| 46.75 | 1000 | | | | |
| 48.00 | 1000 | 0.4225/(1/20) | 0.2865/6 ml | 381.74 | 19.687 |
| 52.17 | 1000 | 0.3655/91/200) | 0.3635/6 ml | 330.15 | 27.700 |
| 56.00 | 1000 | 0.3419/(1/20) | 0.3419/6 ml | 312.11 | 25.314 |

TABLE 8

Reactor Run Data at Temperature of 32° C.

| Time in Hours | Applied Current (milliamps) | $ABS_{500}$/dil. | $ABS_{750}$/sample | $Fe^{++}$ (ppm) | Protein (mg/l) |
|---|---|---|---|---|---|
| 0.00 | — | 0.5735/(1/50) | 0.2147/15 ml | 1240.6 | 4.323* |
| 9.50 | — | 0.3969/(1/50) | 0.1524/15 ml | 860.5 | 2.583 |
| 20.50 | — | 0.1273/(1/10) | 0.2644/10 ml | 57.59 | 8.568 |
| 21.50 | 500 | | | | |
| 24.50 | 500 | 0.0969/(1/10) | 0.1856/5 ml | 44.63 | 8.700 |
| 30.00 | 500 | 0.1232/(1/10) | 0.1650/5 ml | 55.86 | 8.800 |
| 35.00 | 500 | 0.0872/(1/10) | 0.1611/5 ml | 40.49 | 8.470 |
| 36.00 | 750 | | | | |
| 36.30* | 750 | | | 540.19 | 8.470 |
| 45.00 | 750 | 0.1630/(1/11) | 0.2715/5 ml | 80.17 | 17.74 |
| 52.00 | 750 | 0.0835/(1/10) | 0.2400/5 ml | 38.91 | 18.60 |
| 52.60 | 850 | | | | |
| 65.50 | 850 | 0.3279/— | 0.2992/3.9 ml | 14.93 | 23.75 |
| 72.30 | 850 | 0.2358/— | 0.2441/3 ml | 10.39 | 25.73 |

*25 gr $FeSO_4 \times 7H_2O$ added to culture solution.

TABLE 9

Reactor Run Data at Temperature of 36° C. (No electrolysis)

| Time in Hours | Applied Current (milliamps) | $ABS_{500}$/dil. | $ABS_{750}$/sample | $Fe^{++}$ (ppm) | Protein (mg/l) |
|---|---|---|---|---|---|
| 0.00 | | 0.5867/(1/50) | 0.1911/10 ml | 1325.9 | 6.006 |
| 3.50 | | 0.5072/(1/50) | 0.1752/10 ml | 1146.0 | 5.039 |
| 7.75 | | 0.4449/(1/50) | 0.1798/10 ml | 1005.0 | 5.317 |
| 12.00 | | 0.4191/(1/50) | 0.2388/10 ml | 946.59 | 8.908 |
| 17.25 | | 0.4112/(1/50) | 0.1925/10 ml | 928.70 | 6.088 |
| 23.25 | | 0.3251/(1/50) | 0.2000/10 ml | 734.04 | 6.545 |
| 27.25 | | 0.3344/(1/50) | 0.1707/10 ml | 755.04 | 7.763 |

The gradual decrease of ferrous iron (substrate) concentration during the pre-electrolysis part of the runs, as shown in the tables, reflects substrate utilization and that the onset of the stationary phase occurs concomitantly with substrate depletion.

As the data in the tables also demonstrates, initiation of electrolysis consistently caused a resumption of log phase bacterial growth. It was noted that where an initial applied current of relatively low amperage did not cause resumption of log phase growth, an increased current did. (See Table 4). Based on this data, it was concluded that electrolysis improved the growth potential of the organisms.

The data presented in Tables 4–9 next was analyzed to ascertain the optimum temperature for cultivating *T. ferrooxidans* using the above equations, the critical parameters of ferrous iron oxidation rates, protein production rates and yield coefficients for each interval. This data is shown in Tables 10–15.

It first was noted that no significant growth of the organism occurred during the reactor run at 36° C., as seen in Tables 9 and 15. From this, it was concluded that 36° C. was the upper limit for cultivating this organism.

Next, from Tables 10 to 15, the maximum value for each critical parameter for each run was collected and is presented in Table 16.

TABLE 10

Critical Parameter Data for Reactor Run at 24° C. (Table 4)

| Time in Hours | Applied Current (milliamps) | Protein Production (mg/l hr) | Iron Oxidation (mg/l hr) | Yield Coefficient (mg protein/g $Fe^{++}$) |
|---|---|---|---|---|
| 0.00–4.00 | — | −0.285 | 80.10 | −3.557 |
| 4.00–8.00 | — | 0.068 | 78.45 | 0.8668 |
| 8.00–14.25 | — | 0.019 | 44.44 | 0.4275 |
| 14.25–16.75 | — | 0.512 | 30.46 | 16.81 |
| 16.75–20.75 | — | 0.293 | 23.06 | 7.634 |
| 20.75–24.75 | — | 0.845 | 23.06 | 36.64 |
| 24.75–29.00 | — | −0.181 | 16.82 | −10.76 |
| 29.00–32.75 | 250 | 0.108 | 8.84 | 12.22 |
| 32.75–36.75 | 500 | 0.110 | 4.87 | 22.59 |
| 36.75–39.00 | 500 | 0.070 | 30.41 | 2.302 |
| 39.00–40.75 | 500 | 0.465 | 37.33 | 12.46 |
| 40.75–44.75 | 500 | 0.759 | 60.53 | 12.54 |
| 44.75–49.25 | 500 | 0.634 | 62.00 | 10.23 |
| 49.25–52.50 | 500 | 0.574 | 89.70 | 6.399 |
| 52.50–54.50 | 500 | 0.334 | 76.57 | 4.362 |
| 54.50–56.00 | 500 | 0.193 | 118.22 | 1.633 |
| 56.00–60.00 | 800 | 1.320 | 79.16 | 16.68 |
| 60.00–64.50 | 800 | −2.122 | 117.00 | −18.14 |
| 64.50–69.25 | 1200 | −0.168 | 146.72 | −1.145 |

TABLE 11

Critical Parameter Data for Reactor Run at 26° C. (Table 5)

| Time in Hours | Applied Current (milliamps) | Protein Production (mg/1 hr) | Iron Oxidation (mg/1 hr) | Yield Coefficient (mg protein/g $Fe^{++}$) |
|---|---|---|---|---|
| 0.00–5.00 | — | 0.044 | 28.28 | 1.156 |
| 5.00–17.00 | — | 0.118 | 33.88 | 3.348 |
| 17.00–24.00 | — | 0.291 | 76.56 | 3.801 |
| 24.00–30.00 | — | 0.091 | 58.44 | 1.557 |
| 30.00–38.00 | 500 | 0.374 | 54.07 | 6.917 |
| 38.00–43.00 | 500 | 0.194 | 55.29 | 3.509 |
| 43.00–48.50 | 500 | 1.018 | 54.62 | 6.917 |
| 48.50–53.00 | 500 | 0.219 | 64.95 | 3.372 |
| 53.00–59.00 | 750 | 0.797 | 79.51 | 10.02 |
| 59.00–65.50 | 750 | 0.715 | 90.80 | 7.874 |
| 65.50–76.50 | 1000 | 0.281 | 119.89 | 2.344 |
| 76.50–88.50 | 1000 | 0.117 | 123.96 | 0.9439 |

TABLE 12

Critical Parameter Data for Reactor Run at 29° C. (Table 6)

| Time in Hours | Applied Current (milliamps) | Protein Production (mg/1 hr) | Iron Oxidation (mg/1 hr) | Yield Coefficient (mg protein/g $Fe^{++}$) |
|---|---|---|---|---|
| 0.00–2.75 | — | 0.692 | 187.99 | 3.681 |
| 2.75–6.00 | — | 0.036 | 207.03 | 0.1739 |
| 6.00–8.75 | 550 | 0.797 | 84.43 | 9.344 |
| 8.75–12.00 | 550 | 0.704 | 71.61 | 9.831 |
| 12.00–15.00 | 550 | 0.333 | 61.74 | 5.394 |
| 15.00–19.00 | 800 | 0.023 | 86.64 | 0.2658 |
| 19.00–24.25 | 800 | 1.794 | 95.42 | 18.80 |
| 24.25–27.00 | 800 | 0.241 | 102.48 | 2.352 |
| 27.00–29.50 | 1000 | 2.129 | 93.89 | 22.68 |
| 29.50–30.75 | 1000 | −3.810 | 128.47 | −29.66 |
| 30.75–33.75 | 1000 | −1.721 | 129.57 | −13.28 |

TABLE 13

Critical Parameter Data for Reactor Run at 29° C. Using Innoculum of Organisms Cultured under Electrolysis (Pre-adopted) (Table 7)

| Time in Hours | Applied Current (milliamps) | Protein Production (mg/1 hr) | Iron Oxidation (mg/1 hr) | Yield Coefficient (mg protein/g $Fe^{++}$) |
|---|---|---|---|---|
| 0.00–3.50 | — | 0.3804 | 94.57 | 4.023 |
| 3.50–7.00 | — | 0.2420 | 76.91 | 3.147 |
| 7.00–11.00 | — | 0.4340 | 71.98 | 6.030 |
| 11.00–16.00 | — | −0.1552 | 65.02 | −2.337 |
| 16.00–19.50 | 250 | 0.6269 | 17.03 | 36.81 |
| 19.50–23.50 | 250 | 0.6869 | 23.22 | 29.54 |
| 23.50–27.25 | 250 | −0.1352 | 28.70 | −4.711 |
| 27.25–32.00 | 500 | 0.5836 | 12.22 | 47.78 |
| 32.00–36.0 | 500 | −0.4880 | 34.11 | −14.31 |
| 36.00–40.50 | 750 | 1.032 | 48.74 | 21.17 |
| 40.50–45.50 | 750 | −0.9031 | 103.74 | −8.706 |
| 45.50–48.00 | 1000 | 2.772 | 66.22 | 41.87 |
| 48.00–52.17 | 1000 | 1.922 | 136.38 | 14.07 |
| 52.17–56.00 | 1000 | −0.6230 | 128.71 | −4.840 |

TABLE 14

Critical Parameter Data for Reactor Run at 32° C. (Table 8)

| Time in Hours | Applied Current (milliamps) | Protein Production (mg/1 hr) | Iron Oxidation (mg/1 hr) | Yield Coefficient (mg protein/g $Fe^{++}$) |
|---|---|---|---|---|
| 0.00–9.50 | — | −0.103 | 40.10 | −2.569 |
| 9.50–20.50 | — | 0.554 | 72.99 | 7.590 |
| 20.50–24.50 | 500 | 0.033 | 49.74 | 0.6634 |
| 24.50–30.00 | 500 | 0.018 | 59.96 | 0.3002 |
| 30.00–35.00 | 750 | −0.066 | 65.07 | −1.014 |
| 36.25 | 750 | 5 gr $Fe^{++}$ | | |
| 36.25–45.00 | 750 | 1.059 | 124.41 | 8.378 |
| 45.00–52.60 | 750 | 0.123 | 98.89 | 1.244 |
| 52.60–58.75 | 850 | 0.763 | 94.02 | 8.115 |
| 58.75–72.25 | 850 | 0.147 | 109.34 | 1.344 |

TABLE 15

Critical Parameter Data for Reactor Run at 36° C. (No Electrolysis) (Table 9)

| Time in Hours | Applied Current (milliamps) | Protein Production (mg/1 hr) | Iron Oxidation (mg/1 hr) | Yield Coefficient (mg protein/g $Fe^{++}$) |
|---|---|---|---|---|
| 0.00–3.50 | 0 | −0.276 | 51.40 | −5.375 |
| 3.50–7.75 | 0 | 0.654 | 33.18 | 19.71 |
| 7.75–12.00 | 0 | 0.845 | 13.74 | 61.50 |
| 12.00–17.25 | 0 | −0.537 | 3.408 | −157.6 |
| 17.25–23.25 | 0 | 0.0762 | 32.44 | 2.349 |
| 23.25–27.25 | 0 | −0.445 | 37.69 | −11.82 |

TABLE 16

Maxima of Critical Parameters for Reactor Runs

| Temp. (C.) | Maximum Iron Oxidation Rate (mg/1 hr) | Maximum Protein Production Rate (mg/1 hr) | Maximum Protein Concentration (mg/1) | Maximum Yield Coefficient (mg/g) |
|---|---|---|---|---|
| 24 | 118.32 | 1.320 | 25.92 | 36.04 |
| 26 | 123.96 | 1.018 | 24.27 | 18.64 |
| 29 | 129.57 | 2.129 | 33.37 | 22.68 |
| 29* | 136.88 | 2.772 | 27.70 | 47.78 |
| 32 | 126.11 | 1.059 | 25.73 | 8.378 |

*This run was conducted using innoculum cultured under electrolysis.

Table 16 shows that the maximum protein concentration, protein production rate and iron oxidation rate occurred during one of the two 29° C. runs (Tables 6 and 12). However, it also was noted that the maximum protein concentration rate (and thus the maximum protein production rate and the maximum yield coefficient) for the 26° C. run were lower than for the 24° C. run and the 29° C. run. The reason for this is not known. The values for the yield coefficients reflecting the organisms' metabolic efficiency showed no pattern.

The data presented in Table 16 was analyzed further to evaluate the benefit of using innoculum which had been cultured under, or pre-adapted to, electrolysis. This data showed that under electrolysis, each of the maximum critical parameters increased, except the maximum protein concentration. Specifically, when was grown under electrolysis, the maximum yield coefficient increased about 111 percent, the maximum protein production rate increased about 30 percent, and the maximum iron oxidation rate increased about 6 percent.

To verify the positive effect of electrolysis on bacterial growth for each run, the pre-electrolysis maximum critical parameter value and the maximum critical parameter value during electrolysis were expressed in a ratio. This ratio was referred to as an enhancement factor. These data are shown in Table 17. This data generally shows that in each run the higher maximum critical parameters were achieved under electrolysis.

TABLE 17

Ratios of Electrolyzed to Nonelectrolyzed Maximum Critical Parameters

| Temp. (C.) | Maximum Iron Oxidation Rate (mg/l hr) | Maximum Protein Production Rate (mg/l hr) | Maximum Protein Concentration (mg/l) | Maximum Yield Coefficient (mg/g) |
| --- | --- | --- | --- | --- |
| 24 | 1.832 | 1.562 | 2.465 | 0.4552 |
| 26 | 1.619 | 3.498 | 5.082 | 4.904 |
| 29 | 0.6259 | 3.077 | 2.704 | 6.161 |
| 29* | 1.447 | 6.387 | 3.597 | 7.924 |
| 32 | 1.732 | 1.912 | 3.000 | 1.104 |

*Reactor run in which the innoculum was cultured under electrolysis ("pre-adapted").

The data in Table 17 next was analyzed to evaluate the effect on the enhancement factors. It was determined that the effect of electrolysis on the enhancement factor was temperature dependent. It also was determined that using innoculum grown under electrolysis increased the enhancement factor.

The doubling (or generation) time of the organisms in each of the runs also was studied. This data, shown in Table 18, demonstrated that the shortest doubling time was achieved at 29° C. under electrolysis and using pre-adapted organisms.

Conclusions

Based on the above data, it was concluded that the electrolytic bioreactor assembly and method of the present invention makes possible the cultivation of dense cell concentrations of the chemolithotrophic organisms, such as *T. ferrooxidans*. The improved cellular efficiency which occurred with electrolysis is believed to be the result of the cells' ability to make protein using less substrate. This is believed to be so because while cellular efficiency (yield coefficients) increased, the iron oxidation rates showed no significant change either with electrolysis or pre-adapted innoculum. This phenomena probably is due to the continual replenishing of the ferrous iron substrate by the electrolytic reduction of the ferric ions.

There is no substrate depletion typical of non-electrolytic metabolism.

TABLE 18

Minimum Times for Doubling of Cell Count (Protein Concentration)

| Temperature (C.) | Doubling Time Nonelectrolyzed (hrs) | Doubling Time Electrolyzed (hrs) |
| --- | --- | --- |
| 24 | 31.1 | 17.6 |
| 26 | 23.0 | 14.3 |
| 29 | 21.2 | 7.8 |
| 29* | 22.5 | 5.25 |
| 32 | 24.0 | 11.75 |

*Reactor run in which the innoculum was cultured under electrolysis ("pre-adapted").

Rather, under electrolysis the cells "see" a relatively inexhaustible supply of substrate. Based on this, the cells shift from more conservative metabolic mechanisms to mechanisms which utilize externally derived energy. Thus, higher protein production rates are achieved under electrolysis.

It should be noted that cellular efficiency is not a critical factor for coal desulfurization uses of the present invention. For this purpose, the most important parameter is the rate at which the organism can reproduce itself and the rate at which it can oxidize iron. This is true particularly in a leaching type operation where ferrous iron substrate is ubiquitous. When cultivating the organism for seeding purposes, the most important parameter is the maximum cell density (measured by protein concentration) achievable, as dense innoculums would provide a high rate of iron oxidation even if the seeded organisms exhibited a relatively slow growth rate.

Although significantly greater cell densities were obtained using the assembly and method of the present invention, it was noted that there was a point at which even increased current could not overcome a stationary growth phase. The reason for this so-called "crowding" phenomena is not understood fully. It is believed to be caused either by the accumulation of metabclic by-products, other than ferric irons, to toxic levels, or that the higher ferric iron reduction rate required by the greater cell mass exceeded the capabilities of the particular reactor assembly utilized in these studies.

Further, it was concluded that the reactor assembly and method of the present invention could be adpated successfully for microbial desulfurization processes. For example, the reactor assembly could be operated as a continuous stirred-tank reactor (CSTR) run in series with a slurry transport pipeline. As the above data revealed (see Table 18), the present invention utilizing electrolysis provides significantly reduced doubling times of the cells. The minimum doubling time achieved in the present studies, 5.25 hours, corresponds to a potential dilution rate of 0.19 $hr^{-1}$ in a continuous cultivation mode as in a CSTR. This increases the rates of the adsorption-dependent phenomena inherent in such processes. The present invention also is adaptable for growing dense cultures of organisms for use in passive desulfurization processes, such as seeding pre-existing leach dumps and treatment ponds. The present invention also is expected to prove useful in the areas of basic and applied research where dense cultures of such organisms are used.

Changes may be made in the nature, composition, operation and arrangement of the various elements, steps and procedures described herein without departing from the spirit and scope of the invention as defined in the following claims.

What is claimed is:

1. An electrolytic bioreactor comprising:
   a reaction vessel defining a cultivation chamber, adapted for containing a culture solution and a cathode, and an anode chamber disposed in fluid communication with the cultivation chamber, such anode chamber being adapted for containing an electrolyte solution and an anode;
   means for mounting a selective barrier between the anode chamber and the cultivation chamber so that the selective barrier will separate the anode chamber from the cultivation chamber but will allow fluid communication therebetween; and
   a receptacle defining a pH control chamber adapted for receiving samples of the culture solution from the cultivation chamber and connectable by a conduit to the cultivation chamber so that the solution samples within the pH control chamber are insulated from electric current through the cultivation chamber, and being further adapted to cooperate with a pH control system, whereby the pH of the culture solution is monitored and adjusted within the pH control chamber to maintain the culture solution at a selected pH.

2. The electrolytic bioreactor of claim 1 in which the capacity of the anode chamber is about 1% to about 3% of the capacity of the cultivation chamber.

3. The electrolytic bioreactor of claim 1 in which the vessel is a cylinder, the body of which defines the cultivation chamber, and in which the anode chamber is a pocket-shaped space disposed adjacent to and in face to face engagement with a portion of the side wall of the vessel so that the contour of the anode chamber conforms to the contour of the side wall of the vessel and so that a selective barrier, when mounted, will form the inner wall of the anode chamber and a portion of the side wall of the vessel.

4. An electrolytic bioreactor assembly for growing chemolithotrophic organisms, comprising:
   a reaction vessel defining a cultivation chamber, adapted for containing a culture solution, and an anode chamber disposed in fluid communication with the cultivation chamber, such anode chamber being adapted for containing an electrolyte solution;
   a cathode disposed within the cultivation chamber;
   an anode disposed within the anode chamber;
   a selective barrier separating the anode chamber from the cultivation chamber, such barrier being substantially impermeable to the organisms and to cations;
   means for establishing a potential difference between the cathode and the anode; and
   means for maintaining the culture solution within the cultivation chamber at a selected pH, comprising:
     a receptacle defining a pH control chamber, such receptacle adapted for receiving samples of the culture solution;
     means for circulating samples of culture solution from the cultivation chamber through the pH control chamber so that the culture solution samples within the pH control chamber are insulated from electric current within the cultivation chamber;
     means for monitoring the pH of the culture solution within the pH control chamber; and
     means for adjusting the pH of the culture solution within the pH control chamber, such pH adjusting means being responsive to the pH monitoring means.

5. The electrolytic bioreactor assembly of claim 4 further comprising a means for continuously refreshing the electrolyte solution within the anode chamber.

6. The electrolytic bioreactor assembly of claim 5 wherein the means for continuously refreshing the electrolyte solution comprises:
   an electrolyte reservoir adapted for containing fresh electrolyte solution and disposed in fluid communication with the anode chamber;
   means for transferring electrolyte solution from the electrolyte reservoir into the anode chamber;
   an electrolyte catch tank adapted for receiving overflow electrolyte solution from the anode chamber; and
   means for transferring overflow electrolyte solution from the anode chamber to the electrolyte catch tank.

7. The electrolytic bioreactor assembly of claim 4 further comprising a means for maintaining the culture solution within the cultivation chamber at a selected temperature.

8. The electrolytic bioreactor assembly of claim 4 further comprising a means for aerating the culture solution within the cultivation chamber.

9. The electrolytic bioreactor assembly of claim 4 further comprising a stirring means for agitating the culture solution within the cultivation chamber.

10. A method for growing chemolithotrophic organisms capable of oxidizing metal sulfides, comprising:
    contacting the organisms with culture solution comprising metal sulfide substrate within a cultivation chamber of an electrolytic bioreactor assembly wherein a cathode is disposed within the cultivation chamber and wherein an anode is disposed within an anode chamber containing an electrolytic solution, such anode chamber being in fluid communication with the cultivation chamber and separated therefrom by a selective barrier characterized by being substantially impermeable to cations and to the organisms;
    electrolyzing the culture solution and the organisms; and
    maintaining the culture solution at a selected pH during electrolysis by circulating samples of the culture solution through a pH control chamber, so that the culture solution samples within the pH control chamber are insulated from electric current within the cultivaiton chamber, monitoring the pH of the culture solution samples in the pH control chamber, and adjusting the pH of culture solution samples in the pH control chamber in response to such monitoring.

11. The method of claim 10 further comprising refreshing the electrolyte solution in the anode chamber during electrolysis.

12. The method of claim 10 further comprising maintaining the culture solution within the cultivation chamber at a selected temperature during electrolysis.

13. The method of claim 10 further comprising aerating the culture solution within the cultivation chamber during electrolysis.

14. The method of claim 10 further comprising agitating the culture solution within the cultivation chamber during electrolysis.

* * * * *